US008387271B2

(12) United States Patent
Shami et al.

(10) Patent No.: US 8,387,271 B2
(45) Date of Patent: Mar. 5, 2013

(54) HAIR DRYER

(75) Inventors: Farouk M. Shami, The Woodlands, TX (US); Dennis R. Morrison, Seabrook, TX (US)

(73) Assignee: Farouk Systems, Inc., Houston, TX (US)

( * ) Notice: Subject to any disclaimer, the term of this patent is extended or adjusted under 35 U.S.C. 154(b) by 263 days.

(21) Appl. No.: 13/027,146

(22) Filed: Feb. 14, 2011

(65) Prior Publication Data

US 2011/0197466 A1 Aug. 18, 2011

Related U.S. Application Data

(60) Provisional application No. 61/337,939, filed on Feb. 12, 2010, provisional application No. 61/408,642, filed on Oct. 31, 2010.

(51) Int. Cl.
*A45D 20/10* (2006.01)
(52) U.S. Cl. ............... 34/283; 34/97; 601/15; 132/211; 607/91
(58) Field of Classification Search ............ 34/269, 34/283, 97, 99, 100; 132/210, 211, 271; 607/89, 91; 601/7, 10, 15
See application file for complete search history.

(56) References Cited

U.S. PATENT DOCUMENTS

| 6,026,821 | A  | * | 2/2000  | Last ............................ 132/200 |
| 6,199,805 | B1 |   | 3/2001  | Pena |
| 6,378,225 | B1 | * | 4/2002  | Slingo .......................... 34/97 |
| 6,481,116 | B1 | * | 11/2002 | Slingo .......................... 34/97 |
| 7,722,656 | B1 | * | 5/2010  | Segal ............................ 607/91 |
| 2006/0004347 | A1 | * | 1/2006  | Altshuler et al. ................ 606/4 |
| 2007/0027411 | A1 | * | 2/2007  | Ella et al. ....................... 601/7 |
| 2008/0172900 | A1 | * | 7/2008  | Ceva ............................. 34/96 |
| 2008/0215123 | A1 | * | 9/2008  | Maricle et al. ................. 607/89 |
| 2011/0197466 | A1 | * | 8/2011  | Shami et al. .................. 34/283 |
| 2012/0145178 | A1 | * | 6/2012  | Lombardi et al. ............ 132/211 |

FOREIGN PATENT DOCUMENTS

| EP | 1086630 A2 | * | 3/2001 |
| GB | 2211419 A | * | 7/1989 |
| JP | 05220010 A | * | 8/1993 |
| JP | 07051121 A | * | 2/1995 |
| JP | 408047415 A |   | 2/1996 |
| JP | 11285517 A | * | 10/1999 |
| WO | WO 9101473 A1 | * | 2/1991 |
| WO | WO 9926512 A1 | * | 6/1999 |

OTHER PUBLICATIONS

Patent Cooperation Treaty, PCT Written Opinion of the Internation Searching Authority Issued in Connection with Internation Patent Application No. PCT/US10/20392, May 21, 2010; 6 pages.
Patent Cooperation Treaty, PCT Internation Search Report Issued in Connection with International Patent Application No. PCT/US10/20392, May 21, 2010; 5 pages.

* cited by examiner

*Primary Examiner* — Stephen M. Gravini
(74) *Attorney, Agent, or Firm* — George P. Kobler; Lanier Ford Shaver & Payne, P.C.

(57) ABSTRACT

A hair dryer apparatus and method for use in hair care. The apparatus preferably includes a therapeutic housing having at least one near infrared emitting diode, a nozzle, and a housing. Further, disposed within the apparatus may be a circuit board, which is in electronic communication with at least three control buttons, a microprocessor, a liquid crystal display, and a voltage regulator.

20 Claims, 9 Drawing Sheets

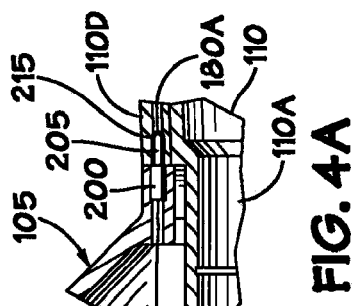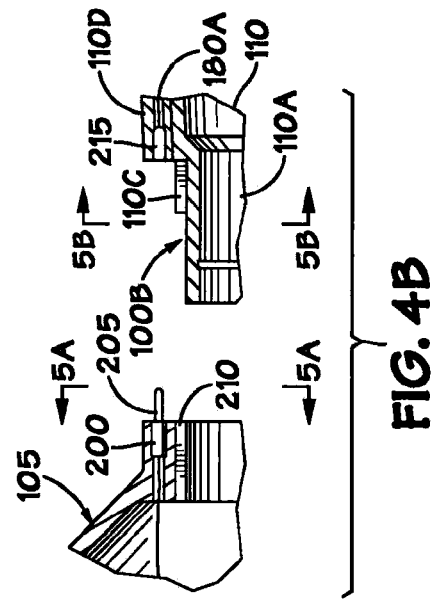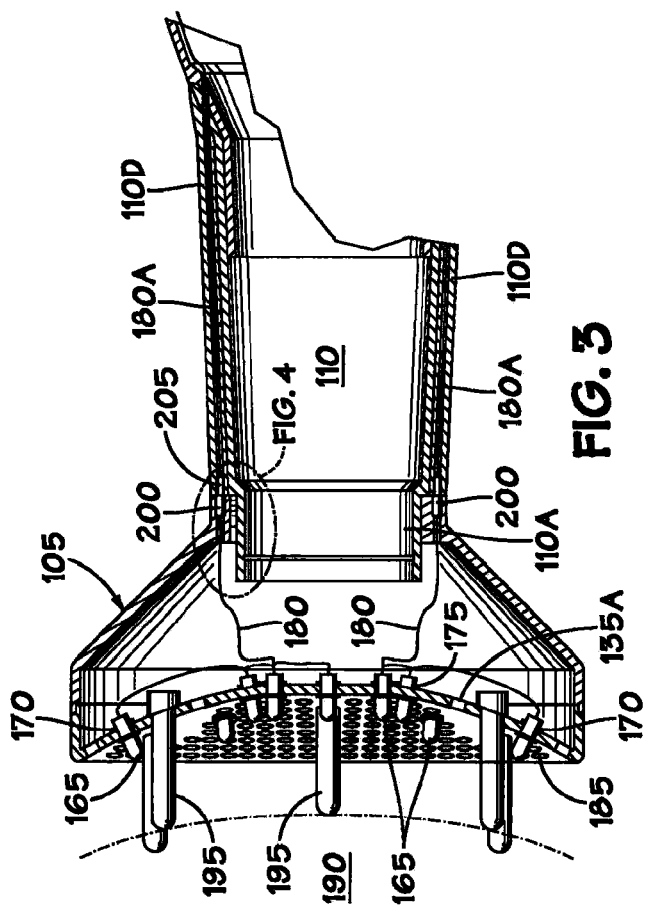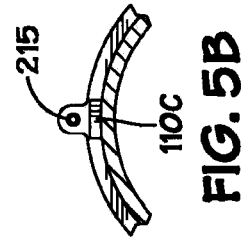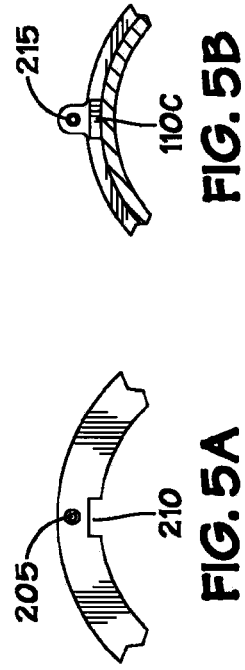

HAIR DRYER

CROSS REFERENCE TO RELATED APPLICATIONS

This application claims the benefit and priority benefit, of U.S. Provisional Patent Application Ser. No. 61/337,939 filed on Feb. 12, 2010 and U.S. Provisional Patent Application Ser. No. 61/408,642 filed on Oct. 31, 2010.

BACKGROUND OF THE INVENTION

1. Field of the Invention

The present disclosure relates generally to the care and enhancement of hair and skin. More specifically, the present disclosure relates to a hair dryer for styling, drying, and enhancing hair, as well as enhancing skin and stimulating the growth of hair follicles.

2. Description of the Related Art

There has long been a desire to dry and style hair, as well as stimulate growth of hair follicles and enhance skin. Prior hair dryers are generally known.

SUMMARY OF THE INVENTION

In accordance with the illustrative embodiments hereinafter described, a hair dryer may include a therapeutic housing having at least one near infrared light emitting diode and a nozzle associated with the therapeutic housing. The hair dryer may further include a housing associated with the nozzle. The housing may contain a fan motor and a fan. The hair dryer may further include a heater assembly associated with the housing, whereby heated air may flow through the nozzle and the therapeutic housing.

According to another illustrative embodiment, the therapeutic housing of the hair dyer may further include a front plate and a cylindrical portion. Alternatively, the therapeutic housing of the hair dyer may further include an outer annular housing ring supported by a plurality of therapeutic housing vanes, and at least one mounting plate member for supporting a plurality of light emitting diodes.

In accordance with another illustrative embodiment, a hair dryer may include a therapeutic housing, a nozzle, a front and rear housing, an end cap, a handle, and an adjustable stand. The therapeutic housing may include at least one near infrared light emitting diode and a collar. The nozzle may have a first end adapted to be received within the collar of the therapeutic housing and a flared end. The front housing may be affixed to the flared end of the nozzle. The rear housing may be affixed to the front housing. The front and rear housing may form a handle and house at least a fan motor and a fan. An end cap may be affixed to the rear housing. The handle may have electrodes, which may be housed within a rigid base. The adjustable stand may comprises a hair stand port for receiving the electrodes.

In accordance with another illustrative embodiment, a method of therapeutic treatment may comprise placing a hair dryer against a target, wherein the hair dryer includes a therapeutic housing having at least one near infrared light emitting diode; using the hair dryer to power the at least one near infrared light emitting diode and emit near infrared light toward the target; and delivering a dose of near infrared light to the target.

While certain embodiments of the present hair dryer will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by the appended claims.

BRIEF DESCRIPTION OF THE DRAWING

The present hair dryer and method of using a hair dryer may be understood by reference to the following description taken in conjunction with the accompanying drawing figures, which are not to scale and contain certain aspects in exaggerated or schematic form in the interest of clarity and conciseness, wherein the same reference numerals are used throughout this description and in the drawing for components having the same structure, and primed reference numerals are used for components having a similar function and construction to those elements bearing the same unprimed reference numerals, and wherein:

FIG. 3 is a partial cross-sectional side view of a portion of the hair dryer according to the illustrative embodiment of the hair dryer of FIG. 1;

FIG. 4A is an enlarged partial cross-sectional view of a portion of the hair dryer as indicated in the phantom lined portion of FIG. 3 denoted as FIG. 4;

FIG. 4B is an enlarged partial cross-sectional view of the portion of the hair dryer of FIG. 4A, illustrating components being disengaged from one another;

FIG. 5A is a partial cross-sectional end view of a component of the hair dryer of FIG. 1 taken along line 5A-5A of FIG. 4B;

FIG. 5B is a partial cross-sectional end view of a component of the hair dryer of FIG. 1 taken along line 5B-5B of FIG. 4B;

DETAILED DESCRIPTION

Figure 1:
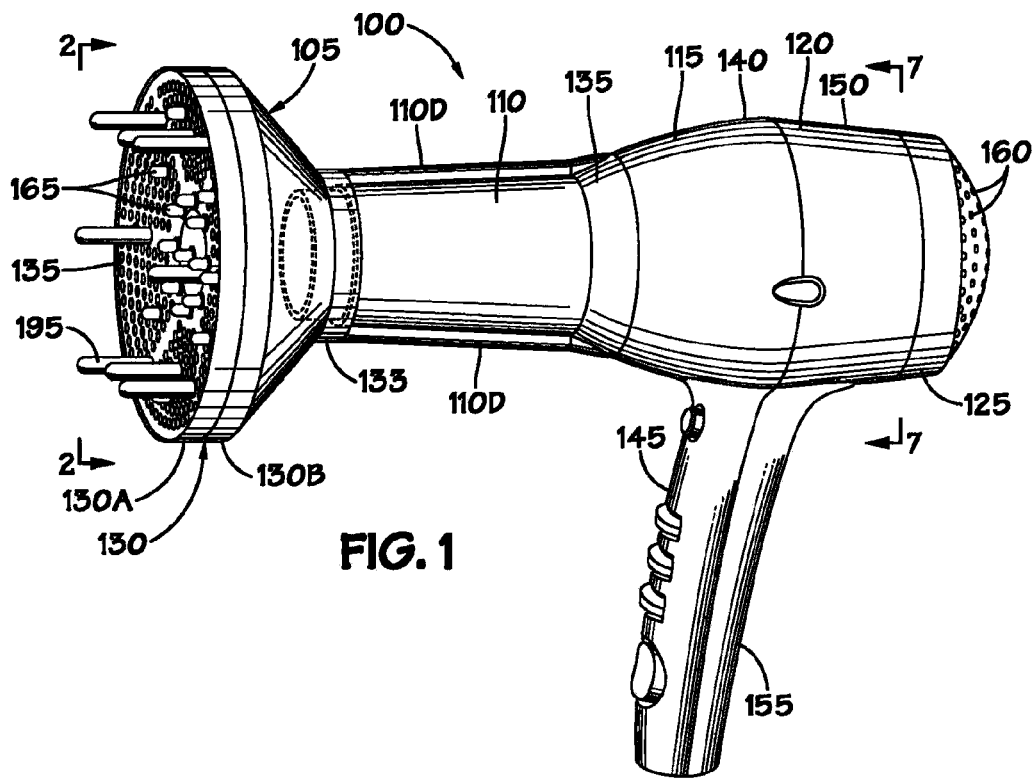
FIG. 1 is a perspective view according to an illustrative embodiment of the present hair dryer.

With reference to FIG. 1, a perspective view of a hair dryer 100 is illustrated. The hair dryer 100 may generally include: a therapeutic housing, or housing, 105, a nozzle 110; a front housing 115; a rear housing 120; and a end cap 125. Preferably, therapeutic housing 105, nozzle 110, front housing 115, rear housing 120, and end cap 125 are made from any suitable material having the requisite strength and heat resistance properties to function in a hair dryer, such as any suitable metal, metal alloy, or plastic material, as are known in the art.

The therapeutic housing 105 may be of a general conical shape and may include a cylindrical portion 130, a collar 133, and a front plate 135. In an embodiment, the therapeutic housing 105, cylindrical portion 130, collar 133, and front plate 135 are integral with each other and formed from a single plastic mold. In an embodiment, the cylindrical portion 130 and the front plate 135 are integral with each other and formed from a single plastic mold, the therapeutic housing 105 and collar 133 are integral with each other and formed from a single plastic mold, and the cylindrical portion 130 and the therapeutic housing 105 may be separate parts affixed to each other by any suitable means, such as glue, screws, mating screw threads, snaps, friction fit, and/or male/female tabs. In an alternative embodiment, the front plate 135 may be integral with a front portion 130a of the cylindrical portion 130, the therapeutic housing 105 may be integral with a rear portion 130b of the cylindrical portion 130, the therapeutic housing 105 may be further integral with the collar 133, and the front portion 130a and rear portion 130b of the cylindrical portion 130 may be affixed to each other by any suitable means, such as glue, screws, mating screw threads, snaps, friction fit, and/or male/female tabs. The therapeutic housing 105 may preferably be affixed or connected to the nozzle 110 by any suitable means, such as glue, screws, mating screw threads, snaps, friction fit, and/or male/female tabs. In an embodiment, disclosed below with reference to FIGS. 3-5B below, the connection between the therapeutic housing 105 and the nozzle 110 may provide an electrical, as well as mechanical, communication or connection between the therapeutic housing 105 and the nozzle 110.

The nozzle 110 may preferably be of a general cylindrical shape and may include a flared end 135 for engagement with the front housing 115. In an embodiment, the nozzle 110 and flared end 135 are integral with each other and formed from a single plastic mold. In another embodiment, the nozzle 110 and flared end 135 may be separate parts affixed to each other by any suitable means, such as glue, screws, mating screw threads, snaps, friction fit, and/or male/female tabs. The nozzle 110 may be affixed to the front housing 115 by any suitable means, such as glue, screws, mating screw threads, snaps, friction fit, and/or male/female tabs.

The front housing 115 may further include a front housing, generally truncated, conical portion 140 and a front handle portion 145 affixed to the front housing truncated conical portion 140. The front handle portion 145, preferably extends downwardly in a direction away from the front housing truncated conical portion 140 to form the front half of the hair dryer's handle. The front housing 115 may be affixed to, or associated with, the rear housing 120 by any suitable means, such as glue, screws, mating screw threads, snaps, friction fit, and/or male/female tabs, to form a housing for the components of the hair dryer 100 as will be hereinafter described.

The rear housing 120 may include a rear housing, generally truncated, conical portion 150 and a rear handle portion 155 affixed to the rear housing truncated conical portion 150. The rear handle portion 155, preferably extends downwardly in a direction away from the rear housing truncated conical portion 150 to form the back half of the hair dryer's handle. In an embodiment, the rear housing truncated conical portion 150 and rear handle portion 155 may be formed integral with each other and formed from a single plastic mold. In another embodiment, the rear housing truncated conical portion 150 and rear handle portion 155 may be separate parts affixed to each other by any suitable means or techniques, such as glue, screws, mating screw threads, snaps, friction fit, and/or male/female tabs. The front handle portion 145 and rear handle portion 155 may be affixed, or secured, to each other by any suitable means, such as glue, screws, mating screw threads, snaps, friction fit, and/or male/female tabs.

The end cap 125 may be affixed to the rear housing 120 by any suitable means, such as glue, screws, snaps, friction fit, and/or male/female tabs. In an embodiment, the rear housing 120 and end cap 125 include mating screw threads such that the end cap 125 may be screwed onto the rear housing 120. Preferably, the end cap 125, includes perforations 160 to allow air to flow into the hair dryer 100.

Figure 2:
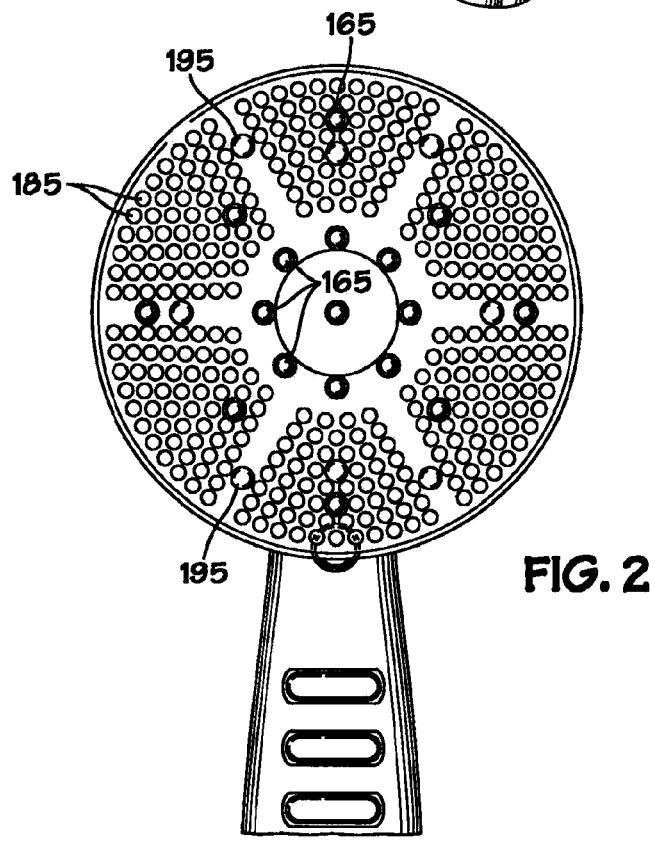
FIG. 2 is a front view of the hair dryer taken along line 2-2 of FIG. 1.

With reference to FIGS. 1-3, the therapeutic housing 105 may have, contain, be disposed about, or affixed to, any number of light-emitting diodes (hereinafter referred to as "LEDs") 165. In an embodiment, the therapeutic housing 105 may include between about 1 and about 100 LEDs, alternatively between about 10 and 35 LEDs 165, and alternatively between about 20 and 32 LEDs 165. In an embodiment, each LED 165 may be disposed within an externally threaded shell 170. The externally threaded shell 170 may be screwed into, and through, a respective cooperating threaded hole or perforation (not shown) of the front plate 135, and optionally secured with an opposing nut 175. LED wires 180 may provide an electrical connection between one or more of the LEDs 165, and may further provide an electrical connection between the LEDs 165 and a power source (described below). In an alternative embodiment, a window, covering, or matting (hereinafter referred to as a "matting" and not shown) may be affixed, for example by glue, staple, or pin, to an interior portion 135a of the front plate 135. The LEDs 165 may be affixed to the matting (not shown) by any suitable means, including without limitation gluing, and aligned with a respective hole or perforation (not shown) of the front plate 135. The matting may be formed of any material, such as plastic, suitable to protect the LEDs 165 from damage and permit a sufficient amount of near infrared light to be passed, or emitted, from the LEDs to outside of the hair dryer 100. In this manner, the LEDs 165 may be completely disposed within the therapeutic housing 105.

In an embodiment, the LEDs 165 may be "powered," connected to a "power source," or otherwise engaged with electrical power received from or through the hair dryer, by an electrical connection between the LEDs and a DC battery supply (not shown) housed within any portion of the hair dryer 100, including without limitation the therapeutic housing 105 through one or more LED wires 180. Alternatively, the LEDs 165 may be "powered," connected to a "power source," or otherwise engaged with electrical power received from or through the hair dryer, by an electrical connection between the LEDs and an AC electricity supply (disclosed hereinafter with reference to FIG. 7) through one or more LED wires 180.

Being powered, the LEDs 165 may emit near infrared light at any wavelength between about 600 nanometers (hereinafter referred to as "nm") and about 1000 nm; alternatively between about 600 and about 900 nm; alternatively between about 600 nm and about 800 nm; alternatively between about 630 nm and 890; and alternately at about 660 nm. In a further embodiment, the LEDs 165 may emit near infrared light at more than one wavelength at the same time. In a non-limiting example, the LEDs 165 may emit near infrared light, at the same time, at about 660 nm and at about 850 nm. Thus, the near infrared light may appear orange, red, or invisible to the naked human eye. LED cooling may be provided by an aluminum heat-sink backing (not shown) disposed for example on, or near, the interior portion 135a of the front plate 135. In an alternate embodiment, the fan (FIG. 7, 265) may be used to draw air across the LEDs 165, or otherwise displace heat generated by the LEDs 165 out of the hair iron 100 through any number of a plurality of front plate vents 185.

Without wishing to be bound by the theory, Applicants believe that application of near infrared light, in sufficient doses, may have many therapeutic benefits, including without limitation, stimulating the growth of hair follicles, reducing facial wrinkles, relieving pain, healing cuts, scrapes and other minor abrasions, as well as acne. Further, without wishing to be bound by the theory, Applicants believe that application of near infrared light, in sufficient doses, may stimulate and/or increase blood flow through capillaries surrounding hair follicles, as well as stimulate and/or increase the vascular endothelial growth factor, otherwise known as VEGF.

In an embodiment, and without wishing to be bound by the theory, each LED 165 may emit near infrared light "diffusively." For example, without limitation, each LED 165 may emit near infrared light with a high intensity at the center of the LED 165, and at a decreasing intensity extending radially outward from the center of the LED 165. Further, without limitation, Applicants believe that the intensity of near infrared light emission between adjacent LEDs 165 may be additive. Thus, without limitation, Applicants believe that by placing adjacent LEDs 165 within sufficient proximity to each other—not too close and not too far—the intensity of emitted near infrared light may remain relatively uniform across various areas. Accordingly, in an embodiment, each LED 165 may be housed within, or affixed to, the therapeutic housing 105 at strategic locations, relative to each other, such that the intensity of light emitted from each LED 165 at the target 190 placed at a distance from the LEDs 165 is relatively uniform. In an embodiment, the intensity of light emitted from each LED 165 at a target 190 placed at a distance from the LEDs 165 is relatively uniform when it remains within plus or minus about 30 percent, alternatively 20 percent, alternatively 10 percent, alternatively 5 percent, alternatively 1 percent, of itself, as measured in areas ranging from about 90 percent to about 10 percent of the area of the therapeutic housing 105. In various embodiments, the target may be a flat sheet-like area. Alternatively, the target area may be generally curved, or otherwise have contours similar to a human head or face. In embodiments wherein the target area is generally curved, the spacing of the LEDs 165 may be adjusted accordingly from the spacing that the LEDs 165 would have otherwise been in had the target area been flat. The target area may be any distance from the therapeutic housing 105. In an embodiment, the target area may be held at a distance from the therapeutic housing 105 at a distance ranging between about 1 millimeter (hereinafter referred to as "mm") and about 1,000 mm, alternatively between about 1 mm and 15 mm, and alternatively between about 6 mm and 15 mm. Front plate protrusions 195, which may be attached to or formed integral with the front plate 135, may assist a user in maintaining the therapeutic housing 105 at a uniform distance against a target 190 during dosing. In an embodiment, front plate protrusions 195 may range in length from about 1 millimeters to about 100 millimeters.

Without wishing to be bound by the theory, Applicants believe that delivering a dose of near infrared light ranging between about 85,000 to about 150,000 micro-Joules/$cm^2$-sec, alternatively between about 90,000 to about 110,000 micro-Joules/$cm^2$-sec, alternatively between about 91,500 to about 105,500 micro-Joules/$cm^2$-sec to the target 190, such as an area of skin, including without limitation a human head, scalp or face, may have therapeutic benefits. In an embodiment, the therapeutic housing 105 may be held against (in other words, at a distance near but not touching) the target 190 (when the LEDs 165 are powered and emitting near infrared light) for a time sufficient for the target 190 to receive a dose of near infrared light ranging between about 85,000 to about 150,000 micro-Joules/$cm^2$-sec, alternatively between about 90,000 to about 110,000 micro-Joules/$cm^2$-sec, alternatively between about 91,500 to about 105,500 micro-Joules/$cm^2$-sec. In an embodiment, the target 190 may receive a dose of near infrared light ranging between about 85,000 to about 150,000 micro-Joules/$cm^2$-sec, alternatively between about 90,000 to about 110,000 micro-Joules/$cm^2$-sec, alternatively between about 91,500 to about 105,500 micro-Joules/$cm^2$-sec within a dosing time ranging from about 1 minute to about 5 minutes, alternatively about 40-50 seconds, alternatively about 42.8 seconds, at a temperature less than about 75° C., alternatively less than about 41° C., alternatively between about 15° C. and 40° C., and alternatively at about 22° C. In an embodiment, a human user may wish to deliver the dose to multiple areas of his, or her, skin or scalp. In an alternative embodiment, a human user may wish to deliver the doses to multiple areas of his, or her, skin or scalp at least one time a day for at least one month. In an alternative embodiment, a human user may wish to deliver the doses to multiple areas of his, or her, skin or scalp at least two times a day for at least six months.

With reference to FIGS. 3-5B, an illustrative non-limiting embodiment of a suitable connection between the therapeutic housing 105 and the nozzle 110 is provided. The LED wires 180 may be electrically led, or connected, from the LEDs 165 to one or more and alternatively two hubs 200. The hubs 200 may be embedded within an annular thickness of the, preferably cylindrical, collar 133, and may terminate in an electrode 205, which may extend beyond the collar 133. The collar 133 may further include a recessed alignment slot 210.

Still with reference to FIGS. 3-5B, a first end 110A of the nozzle 110 may include a recessed portion 110B and one or more alignment members 110C. The nozzle may further include one or more and alternatively two electrode ports 215, which may be embedded within respective channels 110D (additionally illustrated in FIG. 1). The channels 110D, which are preferably integrally formed with the nozzle 110, may run along the length of the nozzle 110 and house electrical wiring 180A, which may connect, or otherwise place into electrical communication, the electrode ports 215 with the remainder of the hair dryer 100. In an embodiment, the therapeutic housing 105 may be engaged with, or affixed to, the nozzle 110 by generally aligning an electrode 205 with a respective electrode port 215 (FIG. 4B). The therapeutic housing 105 may then be slide, pushed, engaged, or otherwise moved, over the recessed portion 110B of the first end 110A of the nozzle 110 until an alignment member 110C pairs with a respective alignment slot 210. Once the alignment member 110C and alignment slot 210 are paired, the therapeutic housing 105 may continue to be slide, pushed, engaged, or otherwise moved, over the nozzle 110 until the electrode 205 communicates with the electrode port 215 to complete an electrical connection between the LED wire 180 and the electrical wiring 180A housed within the channel 110D (FIGS. 3 and 4A).

Figure 6:
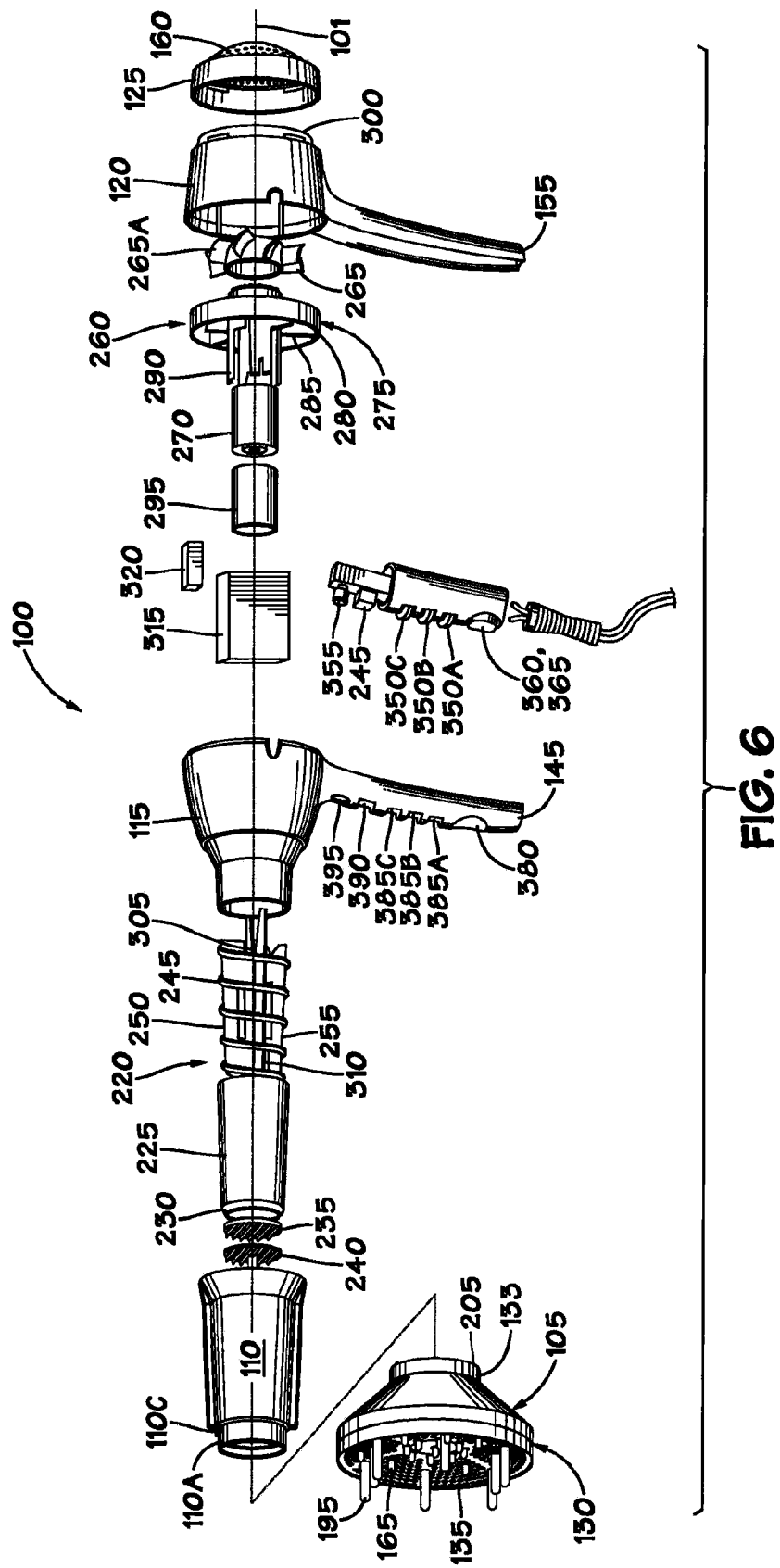
FIG. 6 is an exploded, side view according to the illustrative embodiment of the hair dryer of FIG. 1.

With reference to FIG. 6, an illustrative embodiment of an exploded, perspective view of the hair dryer 100 is provided. As disclosed above, the therapeutic housing 105 may include the cylindrical portion 130, the front plate 135, and the collar 133. The therapeutic housing 105 may be adapted to be engaged with the first end 110A of the nozzle 110. In an embodiment, engagement of the therapeutic housing 105 and the nozzle 110 provides a mechanical connection or communication between the alignment slot 210 (FIG. 5A) and the alignment member 110C, as well as an electrical connection or communication between the LEDs 165 and the remainder of hair dyer 100 through the electrodes 205 and the electrode ports 215.

Still with reference to FIG. 6, the nozzle 110 and at least a portion of the front housing 115 preferably house a heater assembly 220 and its component parts, hereinafter described in greater detail, and a primary thermal insulator 225. The nozzle 110 and at least a portion of the front housing 115 may additionally house: a secondary thermal insulator 230; a ceramic insert 235; and a finger guard 240. The finger guard 240, which is disposed within the first end 110A of nozzle 110, serves to prevent any foreign objects, for example human fingers, from entering the nozzle 110 of the hair dryer 100.

The heater assembly 220 may include a heating element 245 wound about a heating frame 250. The heating frame 250 may be of any shape or cross-sectional configuration, and may be formed from any material having the requisite strength and heat resistance properties for use in a hair dryer, such as a suitable metal, metal alloy, plastic, ceramic, and/or mica material. A preferable configuration of the heating frame 250 is an "X" shaped cross-sectional configuration, when viewed along the longitudinal axis 101 of hair dryer 100. The heating frame is further preferably formed of at least two rectangular-shaped plate members 255, which are disposed substantially perpendicular to each other and substantially disposed in planes coplanar with the longitudinal axis 101 of the hair dryer 100. This configuration may provide rigidity when the heating element 245 is wound about the heating frame 250, and uses a minimal amount of material.

The primary thermal insulator 225, preferably has a generally cylindrical configuration, and may be sized to snugly house, or contain, the heating frame 250, adding further rigidity. The primary thermal insulator 225 may be made from any material having the requisite strength, heat resistance, and insulating properties for use in a hair dryer, such as a suitable metal, metal alloy, plastic, ceramic, and/or mica material. Preferably, the primary thermal insulator 225 insulates the heat, or prevents the heat, generated by the heating element from being readily transmitted to the interior wall surfaces of the nozzle 110 and the front housing 115 to prevent the outer wall surfaces of the nozzle 110 and the front housing 115 from being too hot to the touch of users of the hair dryer 100. The secondary insulator 230 may be further provided to engage and be disposed in a concentric relationship with and within the primary insulator 225. The secondary insulator 230, if present, may serve to assist the primary insulator 225 to prevent the outer wall surfaces of the nozzle 110 and the front housing 115 from being too hot to the touch of users of the hair dryer 100. Additionally, and without wishing to be bound by the theory, the secondary insulator 230, if present, may be made from any material which may reduce any electromagnetic fields ("EMF") emitted by the hair dryer 100, including any extremely low frequency ("ELF") electromagnetic fields emitted by the hair dryer 100. In an embodiment, the secondary insulator 230 may be made from materials such as: a metal selected from the group consisting of steel, iron, gold, silver, and the like; plastic; metal alloy; ceramic; or mica.

Still with reference to FIG. 6, the front housing 115 and rear housing 120 may house, or include, a mounting member 260, a fan 265, and a motor 270, as well as various electrical components, hereinafter described in more detail, and the electrical components may be generally housed between the front handle portion 145 and the rear handle portion 155. Preferably, the mounting member 260 is used to mount the fan 265 and the motor 270 within the hair dryer 100. The mounting member 260 is preferably made from any suitable material having the requisite strength properties to function in a hair dryer, such as such as any suitable metal, metal alloy, or plastic material. Mounting member 260 generally includes a spider member 275 having an outer annular-shaped ring 280 supported by a plurality of vanes 285. Along the longitudinal axis 101 of the hair dryer 100, disposed at the center of the spider member 275, and connected to the vanes 285 may be a generally cylindrical-shaped shaft 290 upon which the fan 265 and motor 270 may be mounted. The ring 280 is preferably snugly received within either the front housing 115, rear housing 120, or both. The generally cylindrical-shaped shaft 290 is further preferably shaped to receive the motor 270 on a forward end of the shaft 290 and the fan 265 on a rear end of shaft 290.

The fan 265 may be made from any suitable material having the requisite strength properties to function in a hair dryer, such as such as any suitable metal, metal alloy, or plastic material. Preferably, the fan 265 may be formed of a plastic material, and the plastic which forms the fan 265 may have a uniform density such that the weight of the fan 265 is balanced; otherwise, modification of the blades of the fan 265 may be required to balance the fan in weight in order to optimize performance while keeping the fan quiet. In an embodiment, the fan blades 265A are preferably thinner at their tip than at the base near the body of the fan 265. The fan 265 may be affixed to the shaft 290 of the mounting member 260 by any suitable means, such as glue, screws, snaps, friction fit, and/or male/female tabs; however, the fan 265 should be able to freely rotate within the hair dryer 100, as by mounting it upon a rotatable shaft (not shown) rotated by the motor 270.

The motor 270 may be a dc motor, but may also be an ac motor. The motor 270 may be affixed to the mounting member 260 by any suitable means, such as glue, screws, snaps, friction fit, and/or male/female tabs. In an alternatively embodiment, a motor cover 295 may be provided about the circumference of the motor 270.

A filter 300 may be disposed within the rear housing 120, preferably external to the rear housing 120 and within the end cap 125. The filter 300 may be made from any suitable material having the requisite filtration properties to function in a hair dryer, such as such as any suitable mesh metal, mesh polymer, mesh fiber, or plastic material. Without wishing to be bound by the theory, the filter 300 acts to keep foreign objects, such as hair, from entering the hair dryer and causing damage to the hair dryer 100 or causing an undesired odor within the hair dryer 100.

Still with reference to FIG. 6, the heater assembly 220 may include: a thermal fuse 305; a bi-metal switch 310; an ion generator 315; and an ozone generator 320. In an alternative embodiment, the heater assembly 220 may include a thermal fuse 305 and a bi-metal switch 310, and the mounting member 260 may include an ion generator 315 and an ozone generator 320. In a still further embodiment, the ion generator 315 and the ozone generator 320 may be associated with, affixed to, or otherwise supported by both the heater assembly 220 and the mounting member 275 and/or the generally cylindrical-shaped shaft 290. In another embodiment, the ion generator 315 may function to produce both ions and ozone and the ozone generator 320 may not present.

The thermal fuse 305 and bi-metal switch 310 may serve to ensure that if the heating element 245 exceeds a pre-determined temperature, the hair dryer 100 shuts off. If the thermal fuse 305 reaches a temperature above a pre-determined temperature, or its set point, the thermal fuse 305 may temporarily disable the electrical current flowing to the heating element 245, causing the hair dryer 100 to cease producing heat until the temperature reaches a safe level. If the bi-metal switch 310 reaches a temperature above its set point, the circuit may permanently break indicating an unsafe condition in the hair dryer 100 and preventing its further use. The set point of the bi-metal switch 310 may be greater than that of the thermal fuse 305.

The ion generator 315 may be any suitable apparatus that is both capable of generating ions and sized to be received within the hair dryer 100. In an embodiment, the ion generator 315 is a spark gap having two, or more, conducting electrodes separated by a gap. The gap may be filled with a gas, such as air. When a voltage ranging between about 200 to about 2000 volts is supplied, a spark may form, and at least a portion of the gas within the gap may become ionized. In this manner, the ion generator 315 may produce ions during the operation of the hair dryer 100. Without wishing to be bound by the theory, Applicants believe that transmitting ions to the hair has advantageous effects on the hair shaft, which make it more manageable.

The ozone generator 320 may be any suitable apparatus that is both capable of generating ozone and sized to be received within the hair dryer 100. In an embodiment, the ozone generator 320 is a high-voltage charged plate having two, or more, charged plates separated by a gap. The gap may be filled with a gas, such as air, or an insulator such as glass or ceramic. When a voltage ranging between about 5500 to about 7000 volts is supplied, at least a portion of the oxygen in the air can form ozone. In this manner, the ozone generator 320 may produce ozone. Without wishing to be bound by the theory, Applicants believe that an accumulation of ozone may sanitize at least a portion of the internal components of the hair dryer 100 as the ozone moves from the ozone generator 310 forward into the nozzle 110 and rearward into the rear housing 120 during a timed sterilization period. The ozone may be moved by either diffusion to accumulate within the housings when the fan 265 is off, or by the fan 265, which may be used to draw air into the hair dryer 100, and blow the air through the hair dryer 100 toward the nozzle 110. Preferably, the ozone generator 320 is operated while the heating element 245 is turned off. Further, Applicants believe without wishing to be bound by the theory that the generation of ozone may produce a generally pleasing odor.

In an alternative embodiment, the ion generator 315 is a spark gap capable of receiving voltage at either a range between about 200 to about 2000 volts or a voltage ranging between about 3300 to about 7000 volts, and thus functions as both an ion generator at low voltage and an ozone generator at high voltage. In embodiments wherein the ion generator 315 can function as both an ion and ozone generator, the ozone generator 320 may be absent. In these embodiments, the ion generator 315 may also produce ozone.

Figure 7:
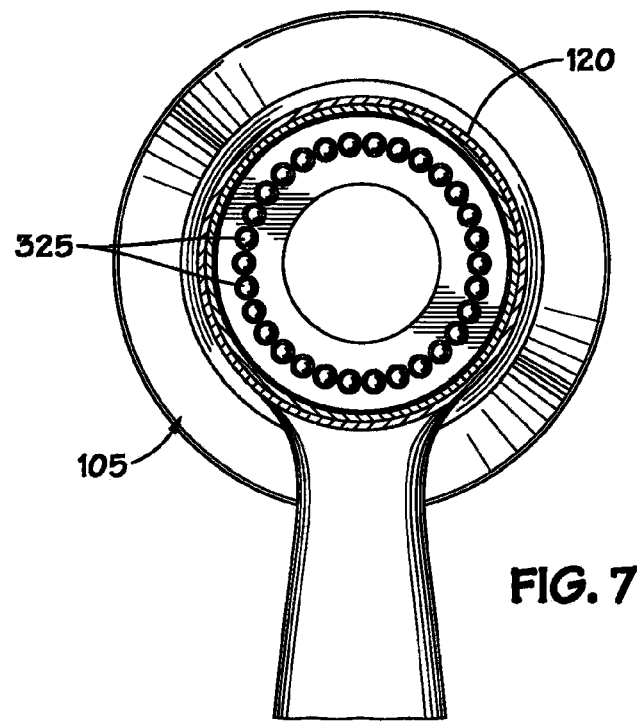
FIG. 7 is a partial cross-sectional view of the hair dryer of FIG. 1 taken along line 7-7 of FIG. 1.

With reference to FIGS. 1 and 7, in an embodiment, one or more, and preferably an array of between about 5 and 15, alternatively between about 5 and 10, ultra-violet light emitting diodes ("UV LED") 325 may be associated with the rear housing 120, as by affixing the UV LEDs 325 to, or otherwise disposing them within, the rear housing 120. Alternatively, the UV LEDs 325 may be mounted in a generally circular array to the back end of the truncated conical portion 150, and oriented to point toward the end cap 125. In an alternative embodiment, the UV LEDs 325 may be oriented to point toward both the end cap 125 and forward toward the fan 265 and nozzle 110. In the embodiment wherein the UV LEDs 325 are oriented toward the fan 265, the blue ultra-violet light emitted from the UV LEDs 325 may sanitize at least a portion of the interior of the housing, the fan blades 265A and all exposed component surfaces disposed between the end cap 125 and the first end 110A of the nozzle 110.

The UV LEDs 325 may emit blue ultra-violet light having wavelengths ranging from about 405 to about 415 nanometers. The blue ultra-violet light may be emitted continuously, in regular pulses, or in irregular pulses. In an embodiment, the intensity of the UV LEDs 325 may be sufficient to kill bacteria, mold, fungus, and certain viruses within about 2 to about 6 hours of exposure, and without negative human eye hazard and without carcinogenic effects. Without wishing to be bound by the theory, Applicants believe that when arranged and oriented to point toward the end cap 125, the blue ultra-violet light emitted from the UV LEDs 325 sanitizes at least a portion of the interior of the end cap 125 and the filter 300 disposed between the end cap 125 and the rear housing 120.

In an embodiment, the UV LEDs 325 may be used in combination with the ozone produced within either the ion generator 315 or the ozone generator 320 to sanitize at least a portion of the interior of the hair dryer 100. In this manner, the hair dryer 100 may be internally sterilized against microbes using two mechanisms: 1) light absorption; and 2) chemical degradation. The microbes susceptible to sterilization may include bacteria, mold, yeast, fungi, and some viruses. Without wishing to be bound by the theory, Applicants believe that the combination of the two sterilization mechanisms has a synergistic effect, thereby sanitizing the interior of the hair dryer 100 with great efficiency.

With reference to FIG. 6, the ceramic insert 235 may be made of a solid ceramic composition. In another embodiment, the ceramic insert 235 may include a ceramic, metal, or plastic core with a coating of polysiloxane and ceramic composition. In an embodiment, the ceramic composition may include at least 16 metal ions in an organic solvent. In another embodiment, the ceramic composition may include metal ions, and preferably at least 16 metal ions suspended in an organic solvent. The 16 metal ions of the ceramic composition may include aluminum, calcium, titanium, chromium, manganese, iron, copper, strontium, barium, lanthanum, cerium, praseodymium, neodymium, lead, thorium, and silicon.

Preferably, the ceramic composition may include about 10.5 aluminum normalized weight percent, based on the total weight percent of metal ions in the ceramic composition, and the normalized weight percent of aluminum may range from between about 0.1 to about 40 percent. Preferably, the ceramic composition may include about 6.7 calcium normalized weight percent, based on the total weight percent of metal ions in the ceramic composition, and the normalized weight percent of calcium may range from between about 1 to about 35 percent. Preferably, the ceramic composition may include about 15.4 titanium normalized weight percent, based on the total weight percent of metal ions in the ceramic composition, and the normalized weight percent of titanium may range from between about 5 to about 55 percent. Preferably, the ceramic composition may include about 10 chromium normalized weight percent, based on the total weight percent of metal ions in the ceramic composition, and the normalized weight percent of chromium may range from between about 1 to about 35 percent.

Preferably, the ceramic composition may include about 1.9 manganese normalized weight percent, based on the total weight percent of metal ions in the ceramic composition, and the normalized weight percent of manganese may range from between about 0.1 to about 45 percent. Preferably, the ceramic composition may include about 7.1 iron normalized weight percent, based on the total weight percent of metal ions in the ceramic composition, and the normalized weight percent of iron may range from between about 2 to about 45 percent. Preferably, the ceramic composition may include about 4.1 copper normalized weight percent, based on the total weight percent of metal ions in the ceramic composition, and the normalized weight percent of copper may range from between about 2 to about 35 percent. Preferably, the ceramic composition may include about 1.1 strontium normalized weight percent, based on the total weight percent of metal ions in the ceramic composition, and the normalized weight percent of strontium may range from between about 0.01 to about 10 percent.

Preferably, the ceramic composition may include about 22.1 barium normalized weight percent, based on the total weight percent of metal ions in the ceramic composition, and the normalized weight percent of barium may range from between about 3 to about 55 percent. Preferably, the ceramic composition may include about 1.9 lanthanum normalized weight percent, based on the total weight percent of metal ions in the ceramic composition, and the normalized weight percent of lanthanum may range from between about 0.1 to about 5 percent. Preferably, the ceramic composition may include about 3.6 cerium normalized weight percent, based on the total weight percent of metal ions in the ceramic composition, and the normalized weight percent of cerium may range from between about 0.1 to about 10 percent. Preferably, the ceramic composition may include about 0.4 praseodymium normalized weight percent, based on the total weight percent of metal ions in the ceramic composition, and the normalized weight percent of praseodymium may range from between about 0.01 to about 5 percent.

Preferably, the ceramic composition may include about 1.3 neodymium normalized weight percent, based on the total weight percent of metal ions in the ceramic composition, and the normalized weight percent of neodymium may range from between about 0.2 to about 10 percent. Preferably, the ceramic composition may include about 0.1 lead normalized weight percent, based on the total weight percent of metal ions in the ceramic composition, and the normalized weight percent of lead may range from between about 0.01 to about 3 percent. Preferably, the ceramic composition may include about 1 thorium normalized weight percent, based on the total weight percent of metal ions in the ceramic composition, and the normalized weight percent of thorium may range from between about 0.01 to about 3 percent. Preferably, the ceramic composition may include about 23.3 silicon normalized weight percent, based on the total weight percent of metal ions in the ceramic composition, and the normalized weight percent of silicon may range from between about 5 to about 45 percent.

Without wishing to be bound by the theory, Applicants believe that when hot air passes over the ceramic insert 235, far infrared heat (thermal waves) are caused to be transferred through the ceramic composition, and, anions, or positive ions, are generated and transmitted to the hair having advantageous effects on the hair shaft, which make it more manageable. Further, without wishing to be bound by the theory, the far infrared heat dries strands of hair from the inside of the strand of hair outwardly to the outside surface of the hair shaft, which is beneficial to the stands of hair by reducing the incidence by which ends of the stands of hair split, i.e., drying hair by far infrared heat reduces split ends.

Figure 8:
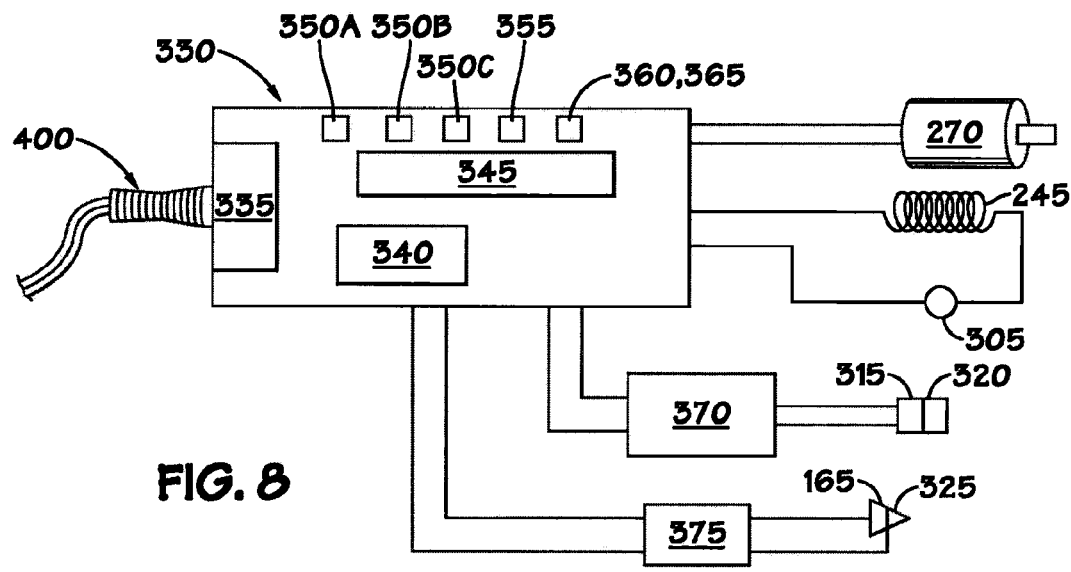
FIG. 8 is a schematic diagram illustrating the electronic circuitry of an illustrative embodiment of the hair dryer of FIG. 1.

With reference to FIG. 8, a circuit board 330 may be associated with, or otherwise housed in the hair dryer 100, such as within the handle formed by the front handle portion (FIG. 6, 145) and the rear handle portion (FIG. 6, 155). The circuit board 330 may by adapted to receive ac current at 120 or 220 volts from a power cord 400, which may be removably connected to a standard wall outlet (not shown), and through a voltage regulator 335 associated with the circuit board 330. In an embodiment, the voltage regulator 335 may be affixed to the circuit board 330. Further, in electrical, or electronic, association with the circuit board 330 may be at least the following elements: at least one microprocessor 340; at least one liquid crystal display ("LCD") 345; at least three and optionally four, five, six or more control buttons, dials, or switches 350A, 350B, and 350C (fourth, fifth, and sixth buttons not shown); a cold shot control button 355; a sterilization, or sanitizing, control dial 360; an infrared control dial 365; at least one high voltage generator 370; and at least one light emitting diode power supply 375.

In an embodiment, the following elements may be affixed to the circuit board 330 and in electrical communication therewith: the voltage regulator 335; the microprocessor 340; at least one LCD 345; at least three buttons, dials, or switches 350A, 350B, and 350C; at least one high voltage generator 370; and at least one LED power supply 375. In an alternative embodiment, due to physical spacing considerations, the at least one high voltage generator 370 and/or the at least one LED power supply 375 may be in electrical communication with the circuit board 330, and disposed elsewhere within the hair dryer 100. In an embodiment, the following components may be in electrical communication with the circuit board 330 and disposed within the hair dryer 100: the heating element 245; the motor 270; the ion generator 315; the ozone generator 320; the thermal fuse 305; and the LEDs 165 and the UV LEDs 325. In an alternative embodiment, the LEDs 165 and UV LEDs 325 may each have a unique LED power supply 375 and may each be in separate electrical communication with the circuit board 330. In a still further embodiment, the LEDs 165 and UV LEDs 325 may each be wired through the other electrical components housed within the hair dryer, including at least the heating element 245; the motor 270; the ion generator 315; the ozone generator 320; the thermal fuse 305. Without wishing to be bound by the theory, Applicants believe that wiring the LEDs 165 and/or the UV LEDs 325 through the other electrical components may provide sufficient electrical resistance to reduce the voltage delivered to the LEDs 165 and/or UV LEDs 325 such that the LED power supply, or voltage regulator, 375 may be omitted.

The front housing 115 may include apertures 380, 385A, 385B, 385C, 390, and 395 through which the following components may be exposed: a cold shot control button 355; a LCD 245; the control buttons, dials, switches, 350A, 350B, and 350C; the sanitizing control dial 360 and the infrared dial 365, respectively. In an embodiment (not shown), the sanitizing control dial 360 and the infrared dial 365 may be separate buttons each having a respective aperture within the front housing 115. Alternatively, the cold shot control button 355, control buttons, dials, or switches 350A, 350B, and 350C, sanitizing control dial 360, and infrared dial 365 may be about level with, or recessed within, respective apertures in the front housing 115. Moreover, in a preferred embodiment, the force to depress each control button may be high enough to minimize unintentional depression of each control button, yet low enough to allow ease of depression. Accordingly, the force needed to depress each control button may range from about 100 grams force to 310 grams force, alternatively from about 150 grams force to about 260 grams force, and alternatively about 200 grams force, plus or minus 50 grams force.

In an embodiment, depressing the cold shot control button 355, may signal the hair dryer 100 to turn on the motor 270, which drives the fan 265 to move relatively cold, or room temperature, air, into the hair dryer 100 and through the nozzle 110. Alternatively, depressing the cold shot control button 355 may send an electrical signal to the motor 270 through the microprocessor 330, which keeps the fan 265 running, and sends an electrical signal to the heating element 245, which turns off, or keeps off, the heating element 245.

Depressing, or rotating, the sanitizing button, or dial, control 360 may activate the sanitization mode, which may send electrical signals through the microprocessor 330 to do the following: 1) deactivate electrical power to the motor 270; 2) deactivate electrical power to the heating element 245; 3) activate the high voltage generator 370, which provides electrical power, ranging from about 5500 volts to about 8000 volts, to the ion generator 315 or the ozone generator 320 to generate ozone; and 4) activate the low voltage LED power supply 375, which provides electrical power, ranging from about 3.0 to about 5.5 volts, to the UV LEDs 325 to emit ultra-violet light. In an embodiment, the microprocessor 330 may have a timing feature and may automatically turns off the UV LEDs 325 and the ozone producing element, either the ion generator 315 or the ozone generator 320, after a predetermined amount of time, ranging between 1 minute and six hours, preferably between two hours and six hours, sufficient to sanitize at least an internal portion of the hair dryer 100. Preferably, the sanitization mode may be stopped before the aforementioned predetermined amount of time by depressing or rotating the sanitizing control button, or dial, 360 a second time.

Depressing, or rotating, the infrared button, or dial, control 365 may activate the infrared mode, which may send electrical signals through the microprocessor 330 to do the following: 1) deactivate electrical power to the motor 270; 2) deactivate electrical power to the heating element 245; and 3) activate the low voltage LED power supply 375, which provides electrical power, ranging from about 3.0 to about 5.5 volts, to the LEDs 165 to emit near-infrared light. In an embodiment, the microprocessor 330 may have a timing feature and may automatically turns off the LEDs 165 after a predetermined amount of time, ranging between 1 second and two hours minutes, alternatively between 30 seconds and two minutes, sufficient to provide a dose of therapeutic treatment to the target (190, FIG. 3) (described above). Preferably, the infrared mode may be stopped before the aforementioned predetermined amount of time by depressing or rotating the infrared control button, or dial, 365 a second time. In an alternate embodiment, the LEDs 165 may be activated while the heating element 245 is also powered so that near infrared light can be applied to the target (190, FIG. 3) while styling. Without wishing to be bound by the theory, the near infrared light may photo-activate, or otherwise stimulate, pre-applied hair treatments or conditioners. The photo-activated hair and scalp conditioners may be formulated to contain special ingredients that absorb the near infrared light, and when activated the conditioner may increase the penetration of color into the hair cuticle. Without wishing to be bound by the theory, this may activate hair lightening compositions and improve circulation in the scalp.

In an embodiment, various control buttons may be assigned a function: an up button 350A, a down button 350B, and a power button 350C. Depressing at least two of the buttons (preferably the up and down buttons) at the same time may trigger a fourth mode function. Alternatively, the fourth mode function may have its own button.

Depressing the power control button 350C may turn the hair dryer 100 on and off. Depressing the mode button, or otherwise engaging the mode function may allow the user to control various functions of the hair dryer 100, including setting the hair dryer 100 to turn off after a set amount of time, setting the hair dryer 100 to turn off after reaching a set temperature, turning the ion generator 315 on, keeping the ion generator 315 on for a certain amount of time, activating the sanitizing mode (described above) through the microprocessor 335, and increasing or decreasing the temperature of the heating element 245. Depressing, or otherwise engaging, the mode button may also allow the user to observe various information, including the current temperature of the heating element 245 in degrees Fahrenheit, Centigrade, Kelvin, or Rankin, the total number of hours and/or minutes that the hair dryer has been used, the total number of hours and/or minutes that the hair dryer has been used during a session, the total amount of hours and/or minutes that the ionic generator has been used, as well as the serial number of the hair dryer.

Depending on the mode that the hair dryer is in, depressing the up button 350A may have different functions. For example, if the hair dryer is in "temperature mode," depressing the up button 350A may increase the temperature of the heating element 245 by a set amount, as regulated by a therimster (not shown), typically one degree, or any other desired increment of temperature. Similarly, if the hair dryer is in "temperature mode," depressing the down button 350B may decrease the temperature of the heating element 245 by a set amount, as regulated by the therimster (not shown), typically one degree, or any other desired increment of temperature. If the thermister fails and the heating element 245 gets too hot, the thermal fuse 305 preferably trips, which causes the hair dryer 100 to turn off.

In another example, if the hair dryer 100 is in "timing mode," depressing the up button 350A may increase the amount of time that the hair dryer will stay on before shutting off, and depressing the down button 350B may decrease the amount of time that the hair dryer will stay on before shutting off. In alternative embodiments, the buttons may be replaced by rotatable dials, switches, and the like.

The power cord 400 may be secured between the lower end of the front handle portion 150 and rear handle portion 160 and provide electrical power via the voltage regulator 335 to the circuit board 330 and the remainder of the electrical components of the hair dryer 100.

Figure 9:
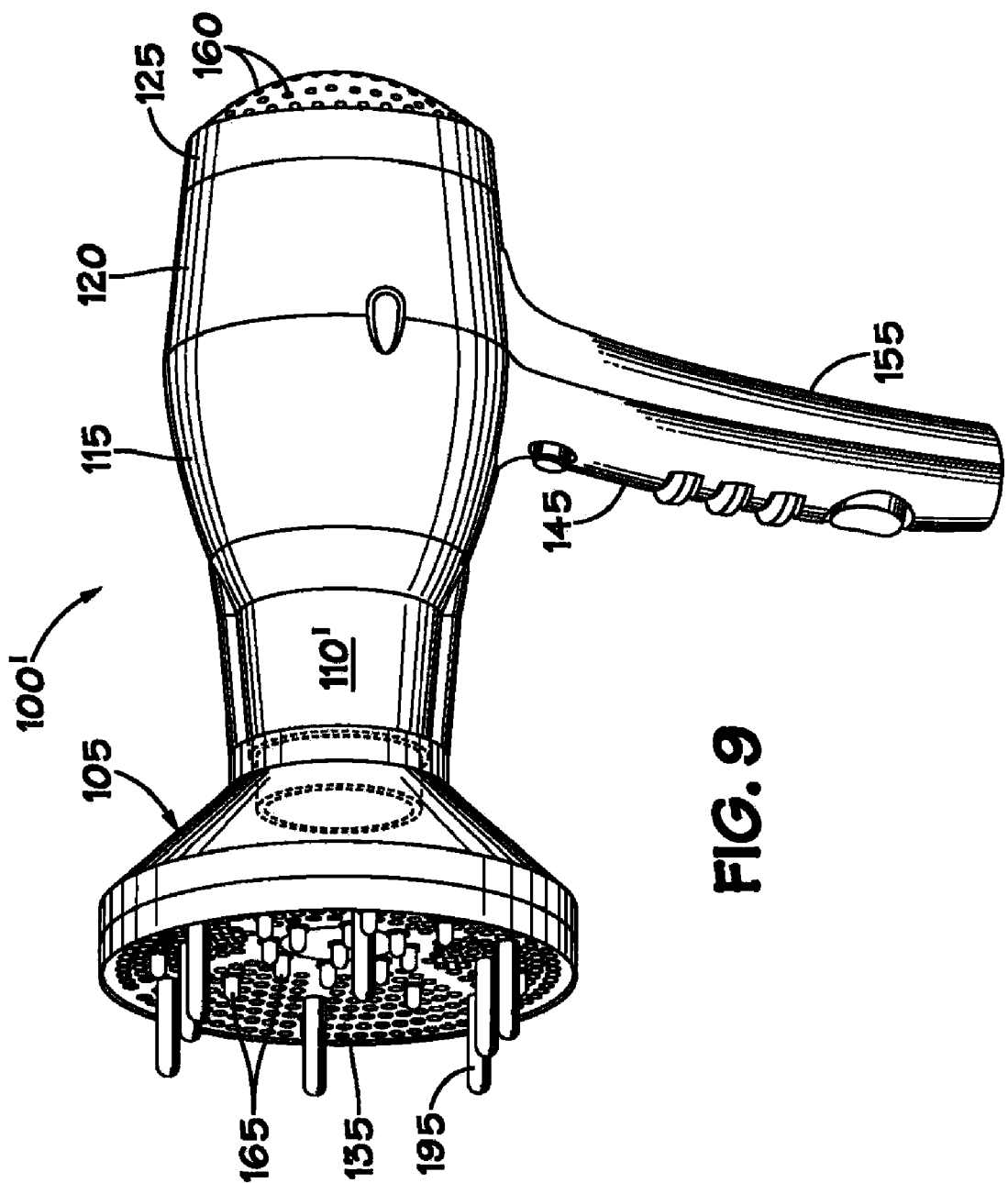
FIG. 9 is a perspective view of an alternative illustrative embodiment of the present hair dryer.
Figure 11:
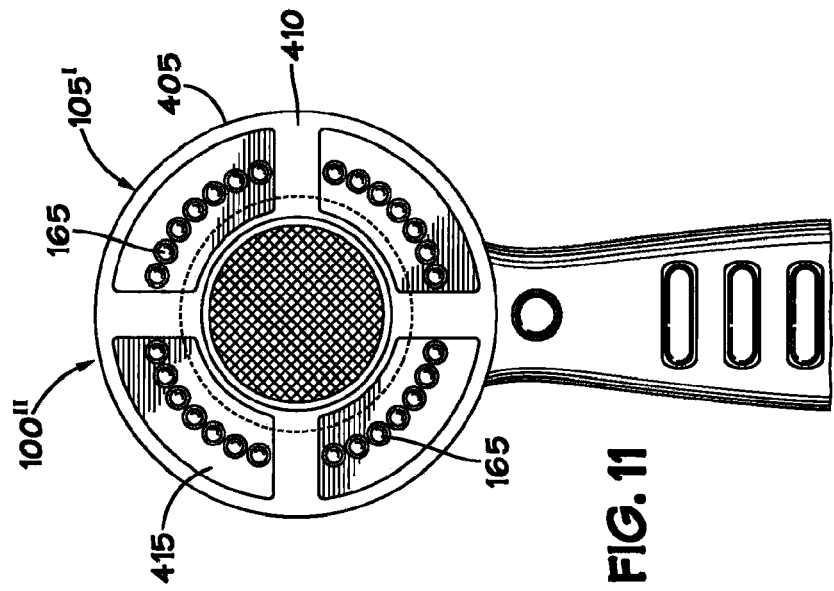
FIG. 11 is a front view of the second alternative illustrative embodiment of the hair dryer of FIG. 10 taken along line 11-11 of FIG. 10.

With reference to FIG. 9, an alternative hair dryer 100' is illustrated. Generally, the alternative hair dryer 100' may be the same in construction and operation as the hair dryer 100, disclosed above with reference to FIGS. 1-8; however, in the alternative hair dryer 100', the physical size of various components, such as for example and without limitation, the length of the nozzle 110' may be reduced. In this manner, the compact, alternative hair dryer 100' may be more easily stored and transported, as compared with the generally larger hair dryer 100, and the alternative hair dryer 100' may be used, without limitation, during travel.

With reference to FIGS. 10-13, a second alternative hair dryer 100" is illustrated. The second alternative hair dryer 100" may generally include: an alternative therapeutic housing 105', the nozzle 110; the front housing 115; the rear housing 120; and the end cap 125. Preferably, the alternative therapeutic housing 105', the nozzle 110, front housing 115, rear housing 120, and end cap 125 are made from any suitable material having the requisite strength and heat resistance properties to function in a hair dryer, such as any suitable metal, metal alloy, or plastic material, as are known in the art.

The alternative therapeutic housing 105' may generally include an outer annular-shaped therapeutic housing ring 405, supported by therapeutic housing vanes 410. The alternative therapeutic housing 105' may be disposed over the first end 110A of the nozzle 110. In an embodiment, the alternative therapeutic housing 105' may engage the nozzle 110 in the same manner as the therapeutic housing 105 engages the nozzle 110. In this manner, the therapeutic housing 105 and the second alternative therapeutic housing 105' may be interchangeable with each other. In an embodiment, the second alternative hair dryer 100" may generally be the same in construction and operation as the hair dryer 100, disclosed with above with reference to FIGS. 1-8; however, in the second alternative hair dryer 100", the alternative therapeutic housing 105' may be different from the therapeutic housing 105, and as further indicated below.

The alternative therapeutic housing 105' may generally include one or more LED mounting plate members 415, which may separate a near infrared portion, or cavity, 420 from an electrical portion, or cavity, 425. In an embodiment, any number of LEDs 165 may be housed or contained with the alternative therapeutic housing 105'. In an embodiment, each LED 165 may be disposed within an externally threaded shell 170. The externally threaded shell 170 may be screwed into, and through, a respective cooperating threaded hole or perforation (not shown) of the LED mounting plate members 415, and optionally secured with an opposing nut 175. In this manner, a forward portion of the LED 165, contained within the externally threaded shell 170, may be housed within the near infrared cavity 420 and a reward portion of the LED 165 may be housed within the electrical cavity 425. In an embodiment, a window, covering, or matting 430 may be affixed, for example by glue, staple, or pin, to the alternative therapeutic housing 105' opposing the LED mounting plate member 415 to enclose the near infrared or cavity 420. The matting 430 may be formed of any material, such as plastic, suitable to protect the LEDs 165 from damage and permit a sufficient amount of near infrared light to be passed, or emitted, from the LEDs to outside of the hair dryer 100.

The LEDs 165 may have LED wires 180, which may be electrically led, or connected, from the LEDs 165 to one or more and alternatively two hubs 200. The hubs 200 may be embedded within the thickness of a rear wall 435 of the alternative therapeutic housing 105', and may terminate in an electrode 205, which may extend beyond the rear wall 435. The rear wall 435 may be generally parallel to and opposing the LED mounting plates 415. In an embodiment, the rear wall 435 further includes a recessed alignment slot (not shown) for engagement with the nozzle. In an embodiment, at least a portion of the rear wall 435 forms the collar 133 (described above with reference to FIG. 1). In a further embodiment, the rear wall 435 and the front end 110A of the nozzle 110 may include a plurality of vents, holes, or perforation, V. Without wishing to be bound by the theory, Applicants believe that when the fan 265 (FIG. 10) is on, it may move air through the nozzle 110 (indicated by the arrows of FIG. 13) and create a force sufficient so as to pull external air through the electrical cavity 425 (indicated by the arrows of FIG. 13), across the LEDs 165 (indicated by the arrows of FIG. 13), and out of the hair dryer 100" (indicated by the arrows of FIG. 13). In this manner, at least a portion of the heat generated by the LEDs 165 may be removed from the electrical cavity 425. Alternatively, Applicants believe, without wishing to be bound by the theory, that the vents, holes, or perforations, V, in the rear wall 435 may permit an exit point for at least a portion of the heat generated by the LEDs 165, even if the fan 265 is not on.

Figure 10:
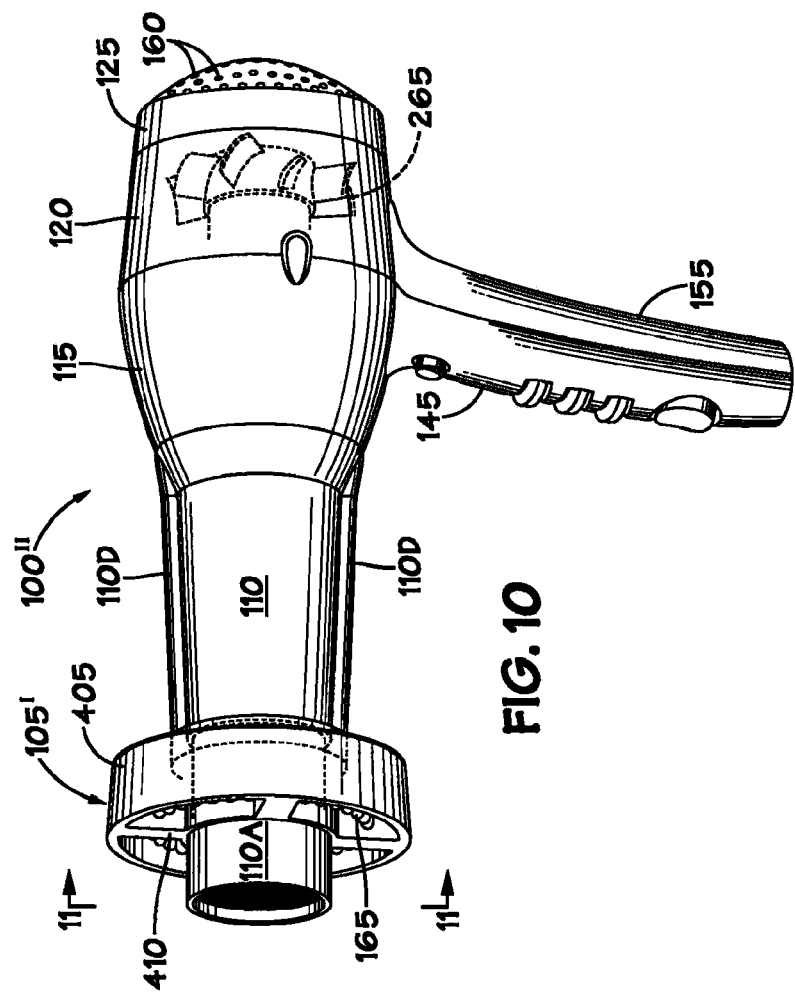
FIG. 10 is a perspective view of a second alternative illustrative embodiment of the present hair dryer.
Figure 12:
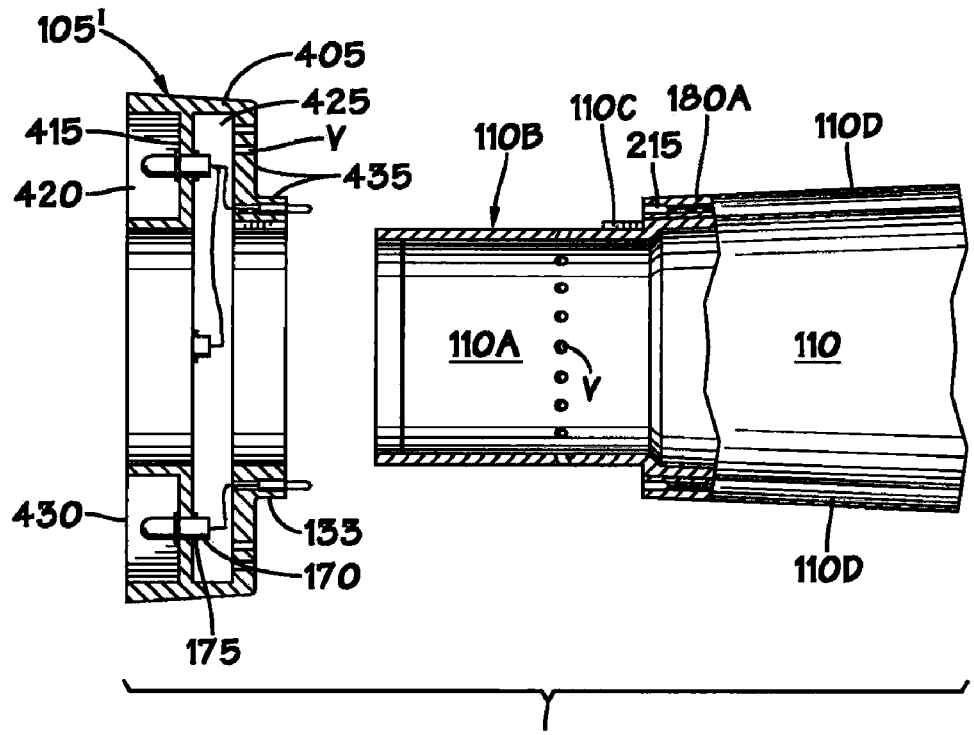
FIG. 12 is a partial cross-sectional side view of a portion of the second alternative illustrative embodiment of the hair dryer of FIG. 10, with certain components being disengaged from one another.
Figure 13:
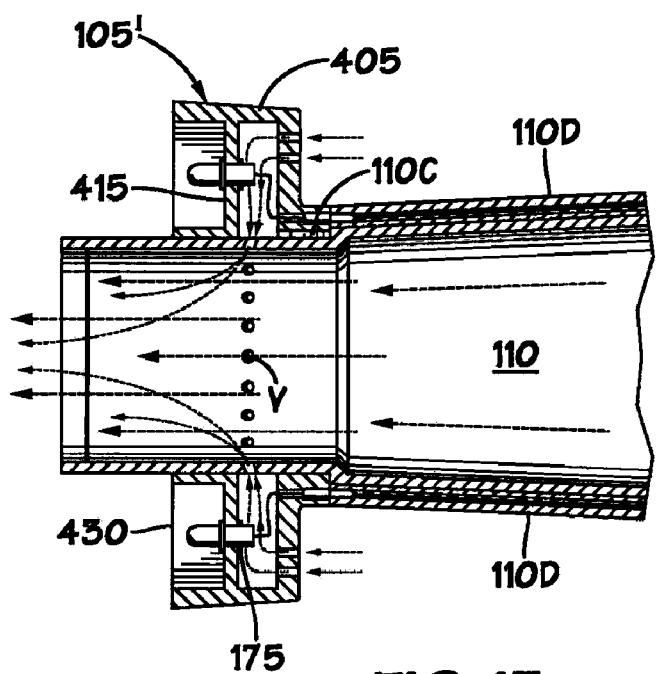
FIG. 13 is an alternative partial cross-sectional side view of a portion of the second alternative illustrative embodiment of the hair dryer of FIG. 10, with certain components being disengaged from one another.

With reference to FIGS. 12-13, the first end 110A of the nozzle 110 may include a recessed portion 110B and one or more alignment members 110C. In an embodiment, an alternative first end 110A of the alternative therapeutic housing 105' may be longer, in length, as compared to the first end 110A of the therapeutic housing 105'. The nozzle 110 may further include one or more and alternatively two electrode ports 210, which may be embedded within respective channels 110D (additionally illustrated in FIG. 10). The channels 110D, which are preferably integrally formed with the nozzle 110, may run along the length of the nozzle 110 and house electrical wiring 180A, which may connect, or otherwise place into electrical communication, the electrode ports 215 with the remainder of the hair dryer 100. In an embodiment, the therapeutic housing 105 may be engaged with, or affixed to, the nozzle 110 by generally aligning an electrode 205 with a respective electrode port 215 (FIG. 4B). The alternative therapeutic housing 105' may be slide, pushed engaged, or otherwise moved, over the recessed portion 110B of the first end 110A of the nozzle 110 until an alignment member 110C pairs with a respective alignment slot 210. Once the alignment member 110C and alignment slot 210 are paired, the alternative therapeutic housing 105' may continue to be slide, pushed engaged, or otherwise moved, over the nozzle 110 until the electrode 205 communications with the electrode port 215 to complete an electrical connection between the LED wire 180 and the electrical wiring 180A housed within the channel 110D (FIGS. 10 and 12).

Figures 14, 14A:
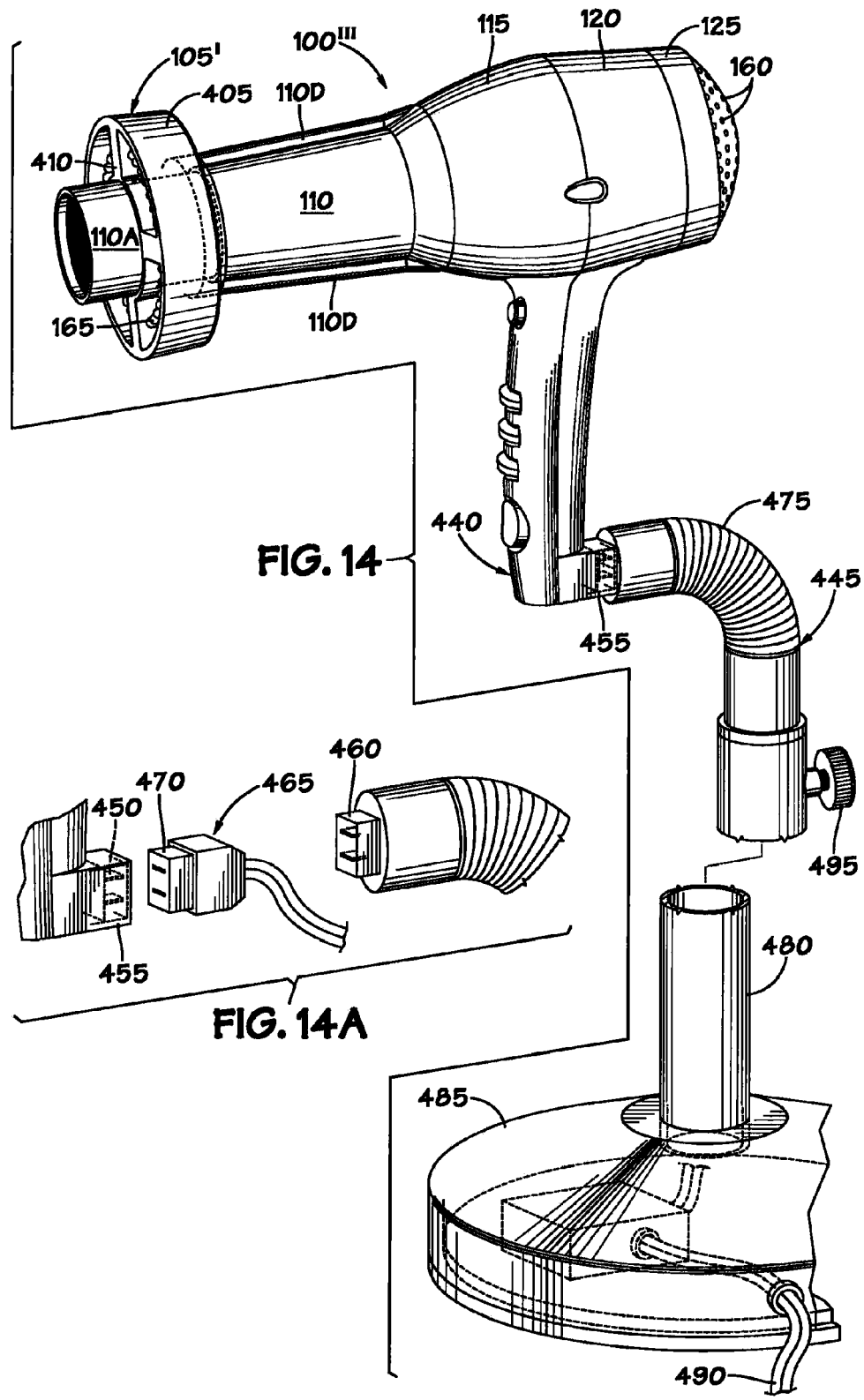
FIG. 14 is a perspective view according to a third alternative illustrative embodiment of the present hair dryer.
FIG. 14A is an exploded perspective view illustrating an embodiment of an electrical connection of the third alternative illustrative embodiment of the hair dryer of FIG. 14.

With reference to FIGS. 14-14A, a third alternative hair dryer 100''' is illustrated. The third alternative hair dryer 100''' may generally include: the therapeutic housing 105 (not shown) or the alternative therapeutic housing 105', the nozzle 110; the front housing 115; the rear housing 120; and the end cap 125. In an embodiment, the third alternative hair dryer 100''' may generally be the same in construction and operation as the hair dryer 100, the alternative hair dryer 100', and second alternative hair dryer 100", disclosed with above with reference to FIGS. 1-13; however, a handle 440 of the third alternative hair dryer 100''' may be adapted to be in electrical and mechanical communication with a cooperating adjustable stand 445. In an embodiment, the handle 440 of the third alternative hair dryer 100''' may include handle electrodes 450, which may be encased or housed within a rigid handle housing 455. Suitable handle housings may be formed of plastics and the like materials having the requisite strength and flexibility to support the weight of the third alternative hair dryer 100'''. In an embodiment, the adjustable stand 445 may include, at a terminal end, a hair stand electrical port or outlet 460, which may receive the electrodes 450 and handle housing 455, and provide both an electrical and mechanical connection between the third alternative hair dryer 100''' and the adjustable stand 445. In an alternative embodiment, the third alternative hair dryer 100''' may be received by a modified electrical plug 465, which may include a plug electrical port or outlet 470 at its first end and a two or three pronged electrical cord at its distal end (not shown). In this embodiment, the third alternative hair dryer 100''' may be plugged into a standard wall outlet (not shown) through the modified electrical plug 465, as opposed to through the hair stand 445.

The adjustable stand 445 a flexible portion 475, a telescoping portion 480, a base portion 485, and a stand electrical cord 490. The flexible portion 475 may be fabricated from a metal flexible conduit or gooseneck so that it may be easily flexed or bent into various configurations. Preferably, the flexible portion 475 may retain its position once placed therein, even under the weight of the third alternative hair dryer 100‴. The telescoping portion 480 may be used to move the third alternative hair dryer 100‴ up and down in a direction generally perpendicular to the base portion 485 (or ground), and may be secured against itself using a knobbed screw, pin, and the like, 495. The base portion 485 may be of a sufficient size and weight to prevent the third alternative hair dryer 100‴ from falling over during use, storage, and adjustment. The stand electrical cord 490 may be plugged into a standard wall outlet (not shown) through which the third alternative hair dryer 100‴ may receive electrical power.

Figure 15:
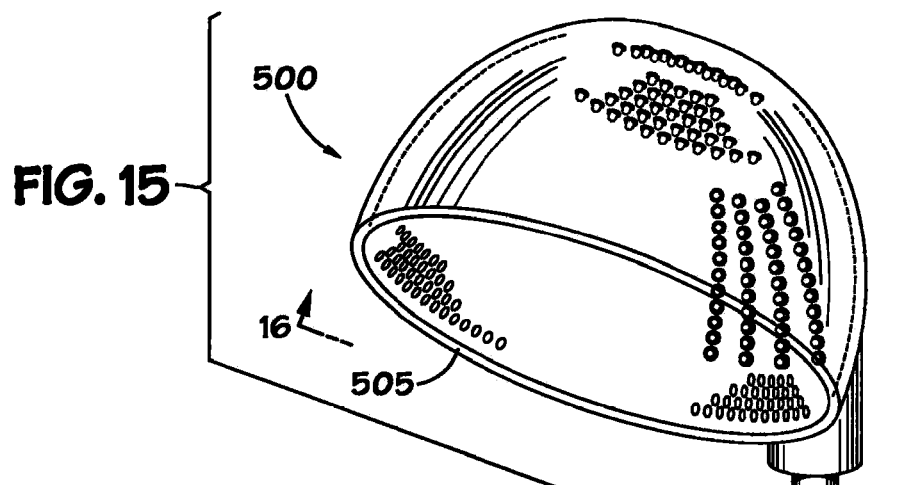
FIG. 15 is a perspective view according to a fourth alternative illustrative embodiment of the present hair dryer.
Figure 16:
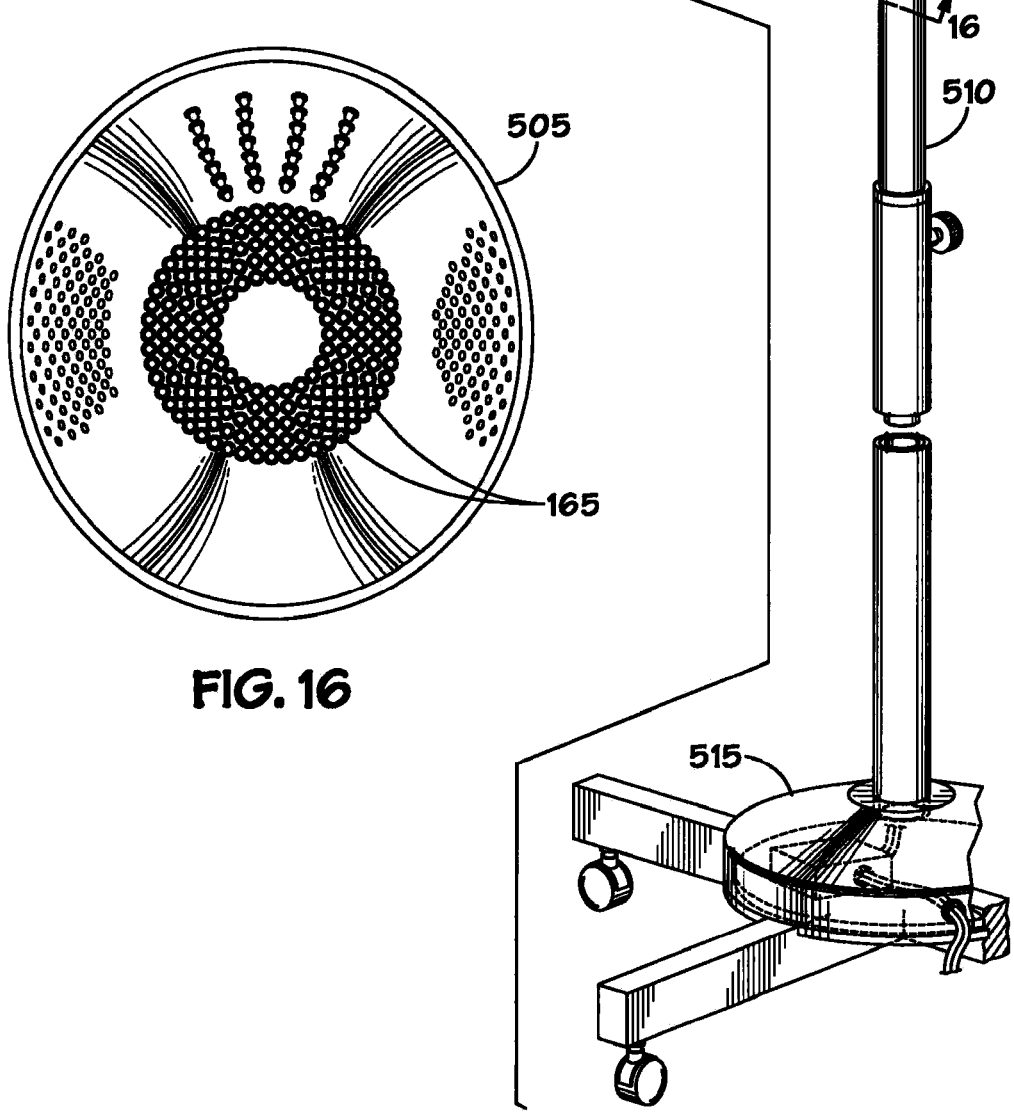
FIG. 16 is an end view of the fourth alternative illustrative embodiment of the present hair dryer of FIG. 15 taken along line 16-16 of FIG. 15.

With reference to FIGS. 15-16, a fourth alternative hair dryer 500 is illustrated. The fourth alternative hair dryer 500 includes a hooded-standing hair dryer modified to incorporate a therapeutic housing 505 having a plurality of LEDs 165 affixed thereto and mounted on a telescoping mast 510. Hair dryer 500 may include a suitable motor, fan, and heating assembly (not shown) within the base 515, mast 510, or housing 505. The internal configurations and further modifications should be understood by one of ordinary skill in the art having the benefit of the present disclosure.

Specific embodiments of the present hair dryer have been described and illustrated. It will be understood to those skilled in the art that changes and modifications may be made without departing from the spirit and scope of the inventions defined by the appended claims.

We claim:

1. A hair dryer comprising:
   a therapeutic housing having at least one near infrared light emitting diode;
   a nozzle associated with the therapeutic housing;
   a housing associated with the nozzle, the housing containing a fan motor and a fan; and
   a heater assembly associated with the housing, whereby heated air may flow through the nozzle and the therapeutic housing.

2. The hair dryer of claim 1, wherein the therapeutic housing further includes a front plate and a cylindrical portion.

3. The hair dryer of claim 1, wherein the front plate further includes and front plate a plurality of front plate protrusions and a plurality of front plate vents.

4. The hair dryer of claim 3, wherein the at least one near infrared light emitting diode is associated with an interior portion of the front plate.

5. The hair dryer of claim 4, wherein the at least one near infrared light emitting diode is in electrical communication with a circuit board housed within the hair dryer.

6. The hair dryer of claim 1, wherein the therapeutic housing further includes an outer annular housing ring supported by a plurality of therapeutic housing vanes, and at least one mounting plate member for supporting a plurality of light emitting diodes.

7. The hair dryer of claim 6, wherein the annular housing ring and nozzle each include a plurality of vents.

8. The hair dryer of claim 1, further including a handle having electrodes, wherein the electrodes are housed within a rigid base, and an adjustable stand, wherein the adjustable stand comprises a hair stand port for receiving the electrodes.

9. The hair dryer of claim 8, wherein the adjustable stand further comprises a flexible portion, a telescoping portion, a base portion, and a stand electrical cord.

10. The hair dryer of claim 1, wherein the therapeutic housing includes a plurality of near infrared light emitting diodes, wherein each near infrared light emitting diode is spaced apart from its adjacent near infrared light emitting diode such that an intensity of near infrared light emitted from the plurality of near infrared light emitting diodes is substantially uniform at a distance from the therapeutic housing.

11. The hair dryer of claim 10, wherein the distance is a length ranging from between about 1 millimeter to about 1,000 millimeters, alternatively from between about 1 millimeter and 15 millimeters.

12. The hair dryer of claim 11, wherein the near infrared light emitting diodes are adapted to deliver a dose of near infrared light ranging between about 85,000 to about 150,000 micro-Joules/cm$^2$-sec, alternatively between about 90,000 to about 110,000 micro-Joules/cm$^2$-sec, alternatively between about 91,500 to about 105,500 micro-Joules/cm$^2$-sec to a target.

13. A method of therapeutic treatment comprising:
   placing a hair dryer against a target, wherein the hair dryer includes a therapeutic housing having at least one near infrared light emitting diode;
   using the hair dryer to power the at least one near infrared light emitting diode and emit near infrared light toward the target; and
   delivering a dose of near infrared light to the target.

14. The method of claim 13, wherein the intensity of near infrared light delivered to the target is substantially uniform.

15. The method of claim 13, wherein the hair dryer further comprises:
   a therapeutic housing having at least one near infrared light emitting diode;
   a nozzle associated with the therapeutic housing;
   a housing associated with the nozzle, the housing containing a fan motor and a fan; and
   a heater assembly associated with the housing, whereby heated air may flow through the nozzle and the therapeutic housing.

16. The method of claim 13, wherein the dose ranges between about 85,000 to about 150,000 micro-Joules/cm$^2$-sec, alternatively between about 90,000 to about 110,000 micro-Joules/cm$^2$-sec, alternatively between about 91,500 to about 105,500 micro-Joules/cm$^2$-sec.

17. The method of claim 16, wherein the target is a human scalp or face.

18. The method of claim 13, wherein the dose of at least about 5 Joules/cm$^2$ of near-infrared light is delivered to a human hair follicle within between about 1 and about 10 minutes.

19. The method of claim 13, further comprising drying human hair while delivering the dose of near infrared light to the target.

20. The method of claim 13, further comprising generating a plurality of ions while delivering the dose of near infrared light to the target, wherein the target is human hair, and the plurality of ions are further delivered to the human hair.

* * * * *